United States Patent [19]
Archibald et al.

[11] Patent Number: 4,772,617
[45] Date of Patent: Sep. 20, 1988

[54] INDOLE DERIVATIVES

[75] Inventors: John L. Archibald, Farnham Royal; Terence J. Ward, Maidenhead, both of England

[73] Assignee: John Wyeth & Brother Limited, Maidenhead, England

[21] Appl. No.: 941,912

[22] Filed: Dec. 15, 1986

[30] Foreign Application Priority Data

Dec. 23, 1985 [GB] United Kingdom ............... 8531665

[51] Int. Cl.$^4$ .................. C07D 209/12; A61K 31/40
[52] U.S. Cl. .................................... 514/323; 546/201
[58] Field of Search ........................ 546/201; 514/323

[56] References Cited

U.S. PATENT DOCUMENTS 3,527,761  9/1970  Archibald et al. .................. 260/293

FOREIGN PATENT DOCUMENTS 1218570  1/1971  United Kingdom .

OTHER PUBLICATIONS

Archibald, et al.: Jour. of Med. Chem., 14, (1971), pp. 1054–1059.

Primary Examiner—Joseph Paul Brust
Attorney, Agent, or Firm—Arthur G. Seifert

[57] ABSTRACT

The invention concerns indole derivatives of formula I

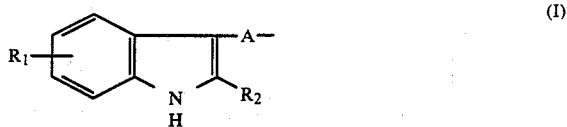

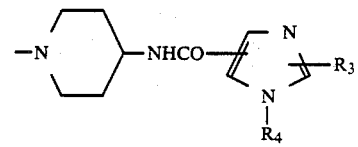

in which
$R_1$ is hydrogen, lower alkyl, halogen, lower alkoxy or hydroxy,
$R_2$, $R_3$ and $R_4$ independently represent hydrogen or lower alkyl,
A represents an alkylene, oxoalkylene or hydroxyalkylene chain each having 2 to 6 carbon atoms or a pharmaceutically acceptable salt thereof, which compounds possess antihypertensive activity while exhibiting reduced CNS depressant properties.

Also disclosed are methods for preparing the compounds of formula I and pharmaceutical compositions containing them.

11 Claims, No Drawings

INDOLE DERIVATIVES

This invention relates to indole derivatives possessing pharmaceutical activity, more particularly to indolyl-piperidine derivatives, processes for their preparation and pharmaceutical compositions containing them.

In our UK Patent Specification No. 1,218,570 there are described and claimed a class of indole derivatives possessing (inter alia) antihypertensive activity and having the formula:

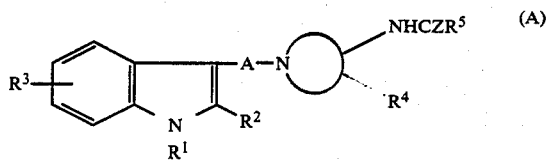

in which formula

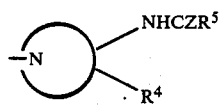

represents a ring system of the general formula

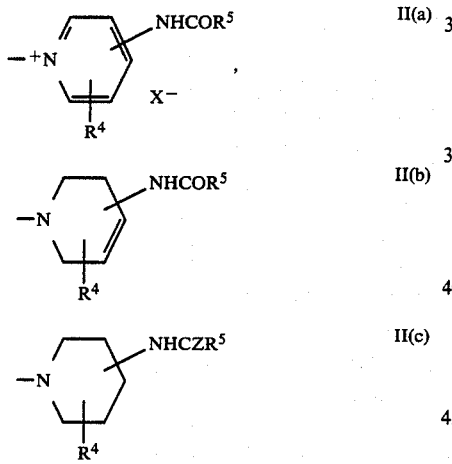

$R^1$ represents hydrogen, lower alkyl, lower aralkyl or aroyl, $R^2$ represents hydrogen, lower alkyl or aryl, $R^3$ represents hydrogen, halogen, lower alkoxy, hydroxy or lower alkyl, $R^4$ represents hydrogen, halogen or lower alkyl, $R^5$ represents aryl (including heterocyclic aryl), lower alkoxy, aryloxy, lower aralkyl, lower aralkyloxy or diaryl-lower alkyl, X is an anion, A represents an alkylene or mono- or di-keto alkylene radical containing up to 4 carbon atoms, and Z is an oxo (i.e.=O) group with the proviso that Z in formula II(c) may also represent two hydrogen atoms when A is alkylene and $R^5$ is aryl.

Examples of heterocyclic aryl groups for $R^5$ were given as 3-indolyl, 2-thienyl and 2-furyl. One of the compounds falling within the scope of formula A is a valuable antihypertensive agent having the generic name indoramin and the chemical name 3-[2-(4-benzamido-1-piperidyl)-ethyl]indole.

Indoramin is used for the treatment of elevated blood pressure in patients and is extensively described in the literature, see—for example "Indoramin in the Treatment of hypertension" The Practitioner, October 1983 Vol. 227. As UK Patent Specification No. 1,218,570 acknowledges the compounds of formula A also possess central nervous system activity and in the case of indoramin such activity is manifest as sedation in a proportion of patients. Latest available figures suggest sedation is not serious but is the main side effect occurring in about 18 percent of patients. It appears to contribute to the withdrawal of only 3.8% of patients which is regarded as very acceptable in the context of antihypertensive treatment. Nevertheless sedation is the dose limiting side effect for indoramin.

We have surprisingly found a class of imidazolyl derivatives falling within the scope of formula A, which compounds possess antihypertensive activity of the same order as indoramin but do not have the same propensity as indoramin to cause depression of the central nervous system. In particular sedation is less likely to occur.

Accordingly this invention provides compounds of formula:

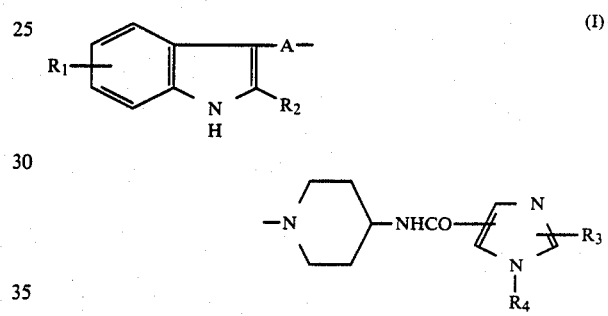

wherein $R_1$ is hydrogen, lower alkyl, halogen, lower alkoxy or hydrogen; $R_2$ represents hydrogen or lower alkyl; A represents an alkylene, oxoalkylene or hydroxyalkylene chain each having 2 to 6 carbon atoms and $R_3$ and $R_4$ independently represent hydrogen or lower alkyl, and pharmaceutically acceptable salts thereof.

By the term lower as used herein is meant groups having 1 to 6 carbon atoms preferably 1 to 4. Examples of lower alkyl groups for each of $R_1$, $R_2$, $R_3$ and $R_4$ are methyl, ethyl, n-propyl and isopropyl.

Examples of lower alkoxy groups for $R_1$ are methoxy, ethoxy, n-propoxy and n-butoxy.

Examples of alkylene chains for A are $-(CH_2)_n-$, $-CO(CH_2)_{n-1}$ and $-CHOH(CH_2)_{n-1}$ in which n is an integer from 2 to 4. Branched chain groups are also included such as

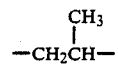

providing such groups contain at least 2 carbon atoms in the main chain linking indole to piperidine. Other examples include

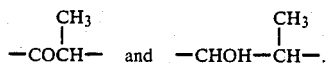

Preferred halogen groups for $R_1$ include chlorine and bromine.

The imidazolyl group is bonded to the —NHCO— group via any of the ring carbon atoms and is preferably imidazol-2-yl or imidazol-4-yl.

The compounds of formula I possess pharmaceutical activity, in particular antihypertensive and/or hypotensive activity when tested on warm blooded animals and hence are indicated for the treatment of high blood pressure.

The compounds of formula I were tested for antihypertensive activity by the following standard procedure:

The blood pressures of male or female spontaneously hypertensive rats are measured in a 37° C. constant temperature housing by means of a tail cuff. Rats with systolic pressures below 155 mmHg are discarded. Groups of rats are dosed orally with the test substance in a suitable vehicle or with vehicle alone. Systolic pressures are recorded before dosing and at selected time points afterwards. Heart rates are derived from caudal artery pulses. Results are analysed statistically by means of 2 way analysis of variance (within group).

In this procedure representative compounds of the invention gave the results shown in the following Table:

The results in Table 1 show that the representative compounds of this invention possess the same order of antihypertensive activity as the commercially available antihypertensive agent indoramin.

The compounds of formula I were also tested for central nervous system activity in mice specifically to determine whether and at what dose levels symptoms associated with sedation were present. The following test procedure was used:

Groups of three female mice (18–25 g) are dosed with the test compound. The usual doses tested are 400, 127, 40 and 12.7 mg/kg and both the oral and intraperitoneal routes are used. The drug is routinely suspended in 5% hydroxypropylmethylcellulose (HPMC).

The animals are observed over a two hour period. The activities looked for during the observation period include:

(i) signs of general stimulation (i.e. increased motor activity, tremor, stereotypy)

(ii) signs of general depression (i.e. decreased motor activity, sedation, hypothermia.

The following results were obtained for representative compounds of formula I:

TABLE 1

| COMPOUND | DOSE/LEVEL (mmol/kg po) | BLOOD PRESSURE as % of pre-dose level (time t after dosing) | |
|---|---|---|---|
| | | t = 2 hrs. | 6 hrs. |
| indol-3-yl-CH₂CH₂N-piperidine-NHCO-(1-Me-imidazol-2-yl) | 0.15 | 53% | 59% |
| | 0.03 | 70% | 84% |
| indol-3-yl-CH₂CH₂N-piperidine-NHCO-(imidazol-2-yl) | 0.15 | 60% | 70% |
| indol-3-yl-CH₂CH₂N-piperidine-NHCO-(imidazol-4-yl) | 0.15 | 67% | 68% |
| indol-3-yl-CH₂CH₂N-piperidine-NHCO-(2-Me-imidazol-4-yl) | 0.15 | | 57% |
| indol-3-yl-CH₂CH₂N-piperidine-NHCO-Ph (indoramin) | 0.15 | 62% | 66% |

TABLE 2

| COMPOUND | Drug level at which following symptoms were first observed (mg/kg) | | |
|---|---|---|---|
| | Sedation | Hypothermia | Decreased Motor Activity |
| ![structure 1] indole-CH₂CH₂N-piperidine-NHCO-imidazole(N-Me) | 127 | 40 | 12.7 |
| ![structure 2] indole-CH₂CH₂N-piperidine-NHCO-imidazole(NH) | 400 | >400 | 40 |
| ![structure 3] indole-CH₂CH₂N-piperidine-NHCO-imidazole(NH) | >400 | >400 | >400 |
| ![structure 4] indole-CH₂CH₂N-piperidine-NHCO-imidazole(Me, NH) | >400 | >400 | 127 |
| indoramin | 40 | 40 | 4 |

The results in Table 2 show the compounds of formula I are much weaker CNS depressants than indoramin requiring much higher dose levels to produce the symptoms of sedation, hypothermia and decreased motor activity. Accordingly the compounds of formula I whilst being as potent as indoramin in lowering blood pressure are much more selective in that they do not have the same propensity to cause depression in the CNS.

This invention also provides processes for preparing the compounds of formula I. In general these methods correspond to those for preparing the compounds of formula A described in UK Patent Specification Nos. 1,218,570, 1,375,836, 1,399,608, 1,543,619 and 1,542,137 and generally involve building up the molecule in known manner from appropriate starting materials comprising reactive substituent groups.

A first process for preparing compounds of formula I comprises acylating a compound of formula

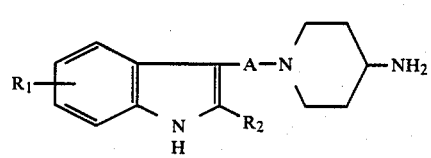

(II)

with an acid of formula

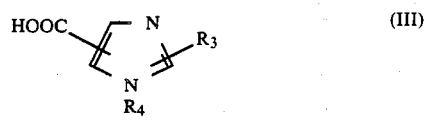

(III)

or a reactive derivative thereof, wherein A, $R_1$, $R_2$, $R_3$ and $R_4$ are as defined above.

As reactive derivatives of the acid of formula III wherein $R_4$ is lower alkyl mention is made of the acid halide, e.g. chloride or an anhydride which derivatives give corresponding compounds of formula I wherein $R_4$ is lower alkyl. Acids of formula III may also be coupled to the amine of formula II by using a coupling reagent such as those well known in the art of peptide chemistry, in particular a carbodiimide e.g. dicyclohexylcarbodiimide. Other reactive derivatives of the acids of formula III include ester derivatives e.g. methyl, phenyl or substituted phenyl esters such as nitro- or halo-substituted phenyl esters. Further derivatives include compounds of formula (IV) in which one of X or Y is N and the other is CH

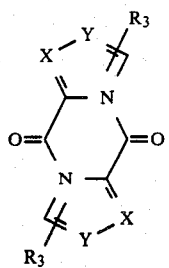

(IV)

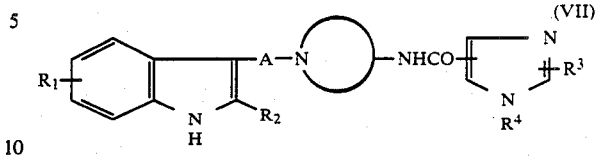

(VII)

wherein

is a ring system of formula (VIIa)

or (VIIb)

wherein R₃ is as defined above, which compounds give corresponding compounds of formula I wherein R₄ is hydrogen.

Compounds of formula IV are prepared by reacting the corresponding imidazole methyl ester with a thionyl halide, e.g. SOCl₂.

In a second general process compounds of formula I may be prepared by reacting a compound of formula

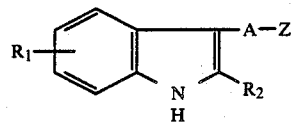

(V)

with a compound of general formula:

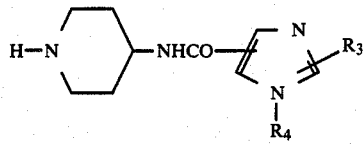

(VI)

in which formulae A, R₁, R₂, R₃, R₄ are as defined above and Z is a halogen atom or an equivalent replaceable radical, e.g. an organic sulphonyl radical such as tosyl. Examples of Z are chlorine, bromine. Alternatively Y can represent OH in which case the reaction may be effected using a catalyst, e.g. Raney nickel according to the procedure set forth in UK Patent Specification No. 1,375,836.

The starting materials of general formula V are known compounds or can be made following the methods known for preparing compounds of this type, e.g. by reducing the corresponding carboxyl compounds followed by halogenation. The starting material of general formula VI can be prepared by forming the oxime of a N-benzyl-4-piperidone, reducing to give the amine, acylating with an acid of general formula

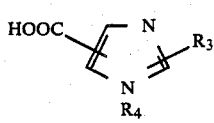

(III)

or a reactive derivative thereof, as described above in connection with the first process, and then hydrogenolysing to replace the N-benzyl group by N-H.

In a third process compounds of formula I may be prepared by reducing compounds of formula A and R₁₋₄ are as defined above and B⊖ is an anion. Methods for carrying out this reduction are extensively described in our UK Patent Specifications Nos. 1218570 and 1542137. For example reduction of either ring system VIIa or VIIb may be carried out using an alkali metal borohydride in a secondary alkanol solvent having 3–5 carbon atoms, e.g. isopropanol. Alternatively reduction may be effected by catalytic hydrogenation, e.g. using palladium on charcoal.

Starting materials of formula VII having a ring system VIIa may be prepared by acylating a 4-aminopyridine with an acid of formula III, or a reactive derivative thereof, and reacting the product with a compound of formula V in the manner described for the first process. Compounds of formula VII having a ring system of formula VIIb can be prepared by reducing a corresponding compound of formula VII having a ring system VIIa using an alkali metal borohydride in methanol solvent. In any of the aforementioned reductions, when A is oxoalkylene, such groups may also be reduced to alkylene or hydroxyalkylene or if desired may be protected by methods known in the art, e.g. by forming a ketal.

Accordingly this invention also provides a further process for preparing compounds of formula I wherein A is lower alkylene or hydroxyalkylene which comprises reducing a compound of formula I wherein A is oxoalkylene.

Yet a further process for preparing compounds offormula I comprises carrying out a Fischer indole synthesis on a compound of general formula

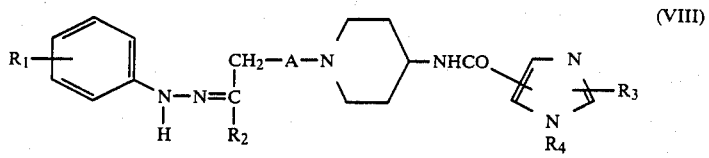

(VIII)

wherein $R_1$, $R_2$, $R_3$, $R_4$ and A are as defined herein above.

The starting material can be prepared by condensing a phenyl hydrazine of formula

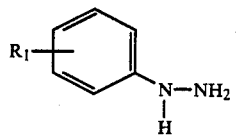

(IX)

with an aldehyde or ketone of general formula

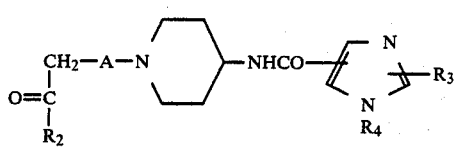

(X)

in which formulae $R^1$, $R^2$, $R^3$, $R^4$ and A are as defined above.

A still further process for preparing a compound of formula I comprises treating a compound of formula XI

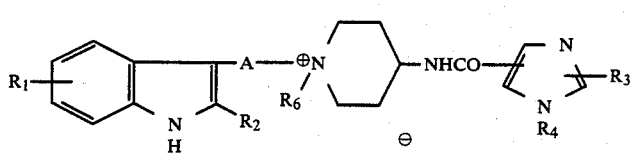

(XI)

wherein $R_{1-4}$, are as defined above, $R_6$ is an organic quaternizing group which can be removed under mild conditions, e.g. hydrogenolysis, and $B^\ominus$ is an anion, under mild conditions effective to remove the group $R_6$. For a description of this process and methods for making compounds of formula XI see UK Patent Specification No. 1,399,608.

Compounds of formula I wherein A is an alkylene chain may be prepared from corresponding compounds of formula I wherein A is $-CO(CH_2)_n-$ by reduction according to the process described in UK Patent Specification No. 1,543,619 using an alkali metal borohydride in a solvent such as alkanols of 2 to 4 atoms, glycol ethers or dioxane.

The reactions outlined above usually are carried out in a solvent which is inert under the reaction conditions, for example an alcohol such as methanol, ethanol or propan-2-ol, ether, dioxane, dimethylformamide, pyridine, water, dimethoxy-ethane, methylene chloride, tetrahydrofuran and acetic acid or mixtures of such solvents. The most suitable solvent system is chosen and varies depending on the particular reactants being employed. If necessary heating the reactants in solution under reflux can be carried out, and if necessary heating under high pressures may also be used.

If necessary, in any of the reactions hereinbefore described, reactive substituent groups may be blocked during a reaction and released at a later stage. As already indicated the novel compounds provided by the invention contain a basic nitrogen atom and thus can form acid addition salts with acids (particularly pharmaceutically acceptable acids) or quaternary ammonium salts, for example with alkyl halides or aralkyl halides (particularly methyl iodide or benzyl chloride or bromide). The acid addition salts may either be formed in situ during the hereinbefore described processes and isolated therefrom or a free base may be treated with the appropriate acid in the presence of a suitable solvent and then the salt isolated. The quaternary salts may be prepared by treating the free base with the appropriate halide in the presence or absence of a solvent.

Examples of acid addition salts are those formed from inorganic and organic acids, such as sulphuric, hydrochloric, hydrobromic, phosphoric, tartaric, fumaric, maleic, citric, acetic, formic, methanesulphonic and p-toluenesulphonic acids.

The invention provides a pharmaceutical composition comprising a compound of formula I or a pharmaceutically acceptable salt thereof in association with a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99%, preferably 10–80% of the active ingredient. Suitable solid carriers are magnesium carbonate, magnesium stearate, talc, lactose, pectin, dextrin starch, gelatin, tragacanth, methylcellulose, sodium carboxymethyl cellulose, a low melting wax and cocoa butter. The term "composition" is intended to include the formulation of an active ingredient with encapsulating material as carrier to give a capsule in which the active ingredient (with or without other carriers) is surrounded by the carrier, which is thus in association with it. Similarly cachets are included. Sterile liquid form compositions include sterile solutions, suspensions, emulsions, syrups and elixirs. The active ingredients can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in suitable organic solvent, for instance aqueous propylene glycol or polyethylene glycol solutions. Aqueous propylene glycol containing from 10 to 75% of the glycol by weight is generally suitable. In other instances other compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilized by intramuscular, intraperitoneal or subcutaneous injection. In many instances a compound is orally active and can be administered orally either in liquid or solid composition form.

Preferably the pharmaceutical composition is in unit dosage form, e.g. as tablets or capsules. In such form, the composition is sub-divided in unit doses containing appropriate quantities of the active ingredients; the unit dosage forms can be packaged compositions, for example packeted powders or vials or ampoules. The unit dosage form can be a capsule, cachet or tablet itself, or it can be the appropriate number of any of these in package form. The quantity of the active ingredient in a unit dose of composition may be varied or adjusted from 5 mg. or less to 500 mg. or more, according to the particular need and the activity of the active ingredient. The invention also includes the compounds in the absence of the carrier where the compounds are in unit dosage form.

The following Examples 1–4 illustrate the invention: Example 5 illustrates the preparation of a starting material.

EXAMPLE 1

N-[1-(2-[1H-indol-3-yl]ethyl)piperidin-4-yl]-1-methyl-1H-imidazole-2-carboxamide A melt of 3-[2-(4-amino-1-piperidyl)ethyl]indole (1.0 g, 4.11 mmol), 2-hydroxypyridine (0.3 g, 3.16 mmol) and 2-methoxycarbonyl-1-methyl-1H-imidazole (0.57 g, 4.07 mmol) was heated at 160° C. for 3 hours under $N_2$. More 2-methoxycarbonyl-1-methyl-1H-imidazole (5 drops) was added and heating continued for a further 1½ hours. The mixture was cooled and chromatographed on silica (100–200 aktiv) eluting with absolute ethanol. The title compound was isolated as a brown glass (0.97 g,).

This was dissolved in hot ethanol (ca. 10 cm$^3$) and ethanolic HCl added to give an acidic solution from which the dihydrochloride of the title compound crystallised on cooling in ice, 0.48 g, m.p. 250°–53° C. (on heating from cold sample gums 140°–160° C., crystallises 225°–40°, starts to decompose at 245° then melts as above).

Analysis: Found: C, 56.60; H, 6.23; N, 16.86% $C_{20}H_{25}N_5O.2HCl$ requires: C, 56.61; H, 6.41; N, 16.50%.

EXAMPLE 2

N-[1-(2-[1H-indol-3-yl]ethyl)4-piperidinyl]-1H-imidazole-2-carboxamide (a) Diimidazo[1,2-a:1',2'-d]tetrahydropyrazine-4,8-dione dihydrochloride (0.32 g, 1.23 mmol) was added to a suspension of 3-[2-(4-amino-1-piperidyl)ethyl]indole (0.59 g, 2.43 mmol) and triethylamine (0.3 g, 2.97 mmol) in dry pyridine (3 cm$^3$). A brown solution was formed which soon crystallised to give a solid mass. After leaving at room temperature for 3 hours the mixture was diluted with water (6 cm$^3$) and the solid collected, washed with water and dried. A second crop was obtained by further dilution of the filtrate, which was combined with the first to give 0.74 g.

The sample was suspended in boiling ethanol (8 cm$^3$) and ethanolic HCl added to give an acidic solution which was cooled in ice to deposit a gum. This was induced to crystallise by squashing vigorously with a spatula; it was collected, washed with ethanol then ether and dried to give 0.86 g of the title compound as the dihydrochloride hemiethanolate mp. 221°–3° C. (gums above 200° C.).

Analysis: Found: C, 55.63; H, 6.64; N, 15.80% $C_{19}H_{23}N_5O.2HCl.\tfrac{1}{2}C_2H_5OH$ requires: C, 55.43; H, 6.51; N, 16.16%.

EXAMPLE 3

N-[(1-(2-[1H-Indol-3-yl]ethyl)piperidin-4-yl]1H-imidazole-4-carboxamide

A mixture of 3-[2-(4-amino-1-piperidyl)ethyl]indole (1.2 g, 5 mmol), acetonitrile (10 cm$^3$), and diimidazo[1,5-a:1',5'-d] tetrahydropyrazine-4,8-dione (0.5 g, excess) was heated at reflux for 0.75 hours. The solvent was evaporated and the solid eluted down a silica column (40 g, Woelm Act () with chloroform/methanol/triethylamine, initially (90:10:0.1 by volume) and finally (75:25:0.1 by volume) to give 0.75 g of product. The base was dissolved in ethanol (8 cm$^3$) and acidified with ethanol HCl, on refrigeration overnight the crystalline title compound was collected 0.8 g as the dihydrochloride salt. Recrystallistion from methanol gave 0.4 g of pure material m.p. 247°–50° C.

Analysis: Found: C, 55.81; H, 5.99; N, 17.07% $C_{19}H_{23}N_5O.2HCl$ requires C, 55.61; H, 6.14; N, 17.07%.

EXAMPLE 4

N-[1-(2-[1H-Indol-3-yl]ethyl)piperid-4-yl]-5-methyl-1H-imidazole-4-carboxamide

Dicyclohexylcarbodiimide (1.24 g, 6 mmol) was added to a stirred solution of 3-[2-(4-amino-1-piperidyl)ethyl]indole (1.2 g, 5 mmol) and 5-methylimidazole-4-carboxylic acid hydrochloride (0.89 g, 5.5 mmol) in pyridine (10 cm$^3$).

A gum precipitated immediately and prevented further stirring. The mixture was allowed to stand 0.5 hours then briefly heated to reflux during which a fine crystalline precipitate formed. The solvent was then evaporated and the residue triturated with hydrochloric acid (2M, 30 cm$^3$ and 10 cm$^3$) and filtered. The filtrate was basified with ammonia to precipitate a brown gum which was collected and washed by decantation. The gum was eluted down a column of silica (30 g) using CHCl$_3$/MeOH/Et$_3$N, initially in the ratio 95:5:0.1 by volume but increasing stepwise to 75:20:0.1 by volume, to give 1 g of the title compound as a foam. This was dissolved in ethanol (10 cm$^3$) and acidified with ethanolic hydrogen chloride to give the dihydrochloride salt 0.76 g, mp 215°–217° C.

Analysis: Found C, 57.00; H, 6.88; N, 16.60% $C_{20}H_{25}N_5O.2HCl$ requires C, 56.60; H, 6.41; N, 16.50%.

EXAMPLE 5

Preparation of diimidazo[1,2-a:1',2-d]tetrahydropyrazine-4,8-dione

A suspension of imidazole-2-carboxylic acid (0.71 g, 6.34 mmol dry, 5.46 mmol monohydrate) in thionyl chloride (6.5 ml) was heated to boiling. Evolution of gas was seen at 60°. Heating was continued for 2 hours to give a pale yellow suspension which was cooled then poured into toluene (23 ml). The solid was collected and washed with ether to give a pale yellow solid 0.60 g. (Dried at 60° C. in vacuo) mp 173°-6° C. (dec).

We claim:

1. A compound of formula

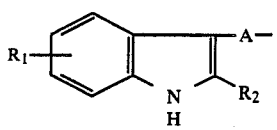

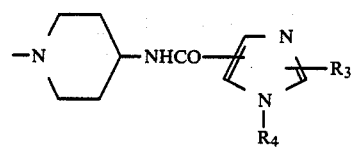

wherein:
  $R_1$ is hydrogen, $C_1$-$C_6$ alkyl, halogen, $C_1$-$C_6$ alkoxy or hydroxy,
  $R_2$, $R_3$ and $R_4$ independently represent hydrogen or $C_1$-$C_6$ alkyl,
  A represents an alkylene, oxalkylene or hydroxyalkylene chain each having 2 to 6 carbom atoms
or a non-hypertensive, pharmaceutically acceptable salt thereof.

2. A compound as claimed in claim 1 wherein A is a chain of formula —$(CH_2)_n$, $CO(CH_2)$—$_{n-1}$ or —$CHOH(CH_2)_{n-1}$ wherein n is an integer from 2 to 4, or A is —$CH_2CH(CH_3)$—, —$COCH(CH_3)$— or —$CHOH.CH(CH_3)$—.

3. A compound as claimed in claim 1 wherein A is —$CH_2CH_2$—.

4. A compound as claimed in claim 1 wherein any of $R_1$, $R_2$, $R_3$, or $R_4$ when $C_1$14 $C_6$ alkyl is methyl, ethyl, n-propyl or isopropyl.

5. A compound as claimed in claim 1 wherein the imidazolyl group is bonded via the 2 or 4 position.

6. A compound as claimed in claim 1 which is N-[1-(2-[1H-indol-3-yl]ethyl)piperidin-4-yl]-1-methyl-1H-imidazole-2-carboxamide or a non-hypertensive, pharmaceutically acceptable salt thereof.

7. A compound as claimed in claim 1 which is N-[1-(2-[1H-indol-3-yl]ethyl)piperidin-4-yl]-1H-imidazole-2-carboxamide or a non-hypertensive, pharmaceutically accetpable salt thereof.

8. A compound as claimed in claim 1 which is N-[1-(2-[1H-indol-3-yl]ethyl)piperidin-4-yl]-imidazole-4-carboxamide or a non-hypertensive, pharmaceutically acceptable salt thereof.

9. A compound as claimed in claim 1 which is N-[1-(2-[1H-indol-3-yl]ethyl)piperid-4-yl]-5-methylimidazole-4-carboxamide or a non-hypertensive, pharmaceutically acceptable salt thereof.

10. A compound as claimed in claim 1 which is in the form of a salt from an acid selected from sulphuric, hydrochloric, hydrobromic, phosphoric, tartaric, fumaric, maleic, citric, acetic, formic, methanesulphonic and p-toluene-sulphonic acid.

11. An antihypertensive pharmaceutical composition comprising an amount effect to lower blood pressure of a compound of formula I:

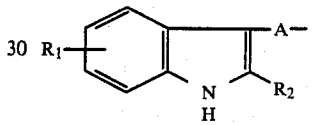

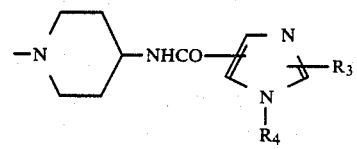

wherein:
  $R_1$ is hydrogen, $C_1$-$C_6$ alkyl, halogen, $C_1$-$C_6$ alkoxy or hydroxy,
  $R_2$, $R_3$ and $R_4$ independently represent hydrogen or $C_1$-$C_6$ alkyl,
  A represents an alkylene, oxoalkylene or hydroxyalkylene chain each having 2 to 6 carbon atoms
or a non-hypertensive, pharmaceutically acceptable salt thereof and a pharmaceutically acceptable carrier.

* * * * *